US005853722A

United States Patent [19]
Rollins et al.

[11] Patent Number: 5,853,722
[45] Date of Patent: Dec. 29, 1998

[54] USE OF C5-SPECIFIC ANTIBODIES FOR REDUCING IMMUNE AND HEMOSTATIC DYSFUNCTIONS DURING EXTRACORPOREAL CIRCULATION

[75] Inventors: Scott Rollins, Monroe; Brian R. Smith, Madison; Stephen P. Squinto, Bethany, all of Conn.

[73] Assignees: Alexion Pharmaceuticals, Inc.; Yale University, both of New Haven, Conn.

[21] Appl. No.: 575,057

[22] Filed: Dec. 21, 1995

Related U.S. Application Data

[63] Continuation of Ser. No. 217,391, Mar. 23, 1994, abandoned.
[51] Int. Cl.$^6$ .......................... A61K 39/395; C07K 16/36
[52] U.S. Cl. .................................. 424/145.1; 424/140.1; 530/387.29; 530/389.3
[58] Field of Search ............................. 424/130.1, 140.1, 424/145.1; 530/387.1, 388.1, 388.25, 389.1, 389.3

[56] References Cited

U.S. PATENT DOCUMENTS

| | | |
|---|---|---|
| 4,686,100 | 8/1987 | Raffin et al. . |
| 5,135,916 | 8/1992 | Sims et al. .................................. 514/21 |
| 5,506,247 | 4/1996 | Sindelar et al. . |

OTHER PUBLICATIONS

Harris et al. Tib Tech 11:42–45 (1993).
Wurzner et al. Complemt. inflamm 8:328–340 (1981).
Mollnes Ann Thorac Surg 52:92–7 (1991).
Bator et al. Mediators of Inflammation 2:135–141 (1993).
Videm et al. J. Thorac Cardiovasc Surg 101:654–60 (1991).
Altieri, et al., "Adhesive receptor Mac–1 coordinates the activation of factor X on stimulated cells of monocytic and myeloid differentiation: An alternative intiation of the coagulation protease cascade" Proc Natl Acad Sci USA 85:7462–7466, 1988.
Arnaout, et al. "Increased Expression of an Adhesion–Promotion Surface Glycoprotein in the Granulocytopenia of Hemodialysis" N Engl J Med 312:457–462, 1985.
Arnaout, "Structure and Function of the Leukocyte Adhesion Molecules CD11/CD18" Blood 75:1037–1050, 1990.
Aslan, et al., "The factors effecting complement activation in open heart surgery" J Cardiovasc Surg 33:754–760, 1992.
Bidstrup, et al., "Reduction in blood loss and blood use after cardiopulmonary bypass with high dose aprotinin (TrasyL0L)" J Thorac Cardiovasc Surg 973:364–372, 1989.
L. Casey, "Role of Cytokines in the Pathogenesis of Cardiopulmonary–Induced Multisystem Organ Failure" Ann Thorac Surg 56:S92–6, 1993.
Cavarocchi, et al., "Complement activation during cardiopulmonary bypass" J Thorac Cardiovasc Surg 91:252–258, 1986.
Cavarocchi, et al., "Oxygen free radical generation during cardiopulmonary bypass: correlation with complement activation" Circulation 74 (suppl III) :130–133, 1986.

Chenoweth, et al., "Complement Activation during Cardiopulmonary Bypass" N Eng J Med 304:497–502 1981.
D. Chenoweth, "Anaphylatoxin Formation in Extracorporeal Circuits" Complement 3:152–165, 1986.
Chiu, et al., "Complement (C3, C4) Consumption in Cadiopulmonary Bypass, Cardioplegia, and Protamine Administration" Ann Thorac Surg 37:229–232, 1984.
Copeland, et al., "Bleeding and Anticoagulation" Ann Thorac Surg 47:88–95, 1989.
Cosgrove, et al., "Aprotinin Therapy for Reoperative Myocardial Revascularization: A Placebo–Controlled Study" Ann Thorac Surg 54:1031–38, 1992.
Dreyer, et al., "Neutrophil Accumulation in Ischemic Canine Myocardium: Insights into Time Course, Distribution, and Mechanism of Localization During Early Reperfusion" Circ 84:400–411, 1991.
Finn, et al., "Interleukin–8 release and neutrophil degranulation after pediatric cardiopulmonary bypass" J Thorac Cardiovasc Surg, 105:234–241, 1993.
Furie, et al., "E–Selectin (Endothelial–Leukocyte Adhesion Molecule–1) Is Not Required for the Migration of Neutrophils across IL—1—Stimulated Endothelium in Vitro" J Immunol 148:2395–2404, 1992.
Gillinov, et al., "Complement Inhibition With Soluble Complement Receptor Type 1 in Cardiopulmonary Bypass" Ann Thorac Surg 55:619–624, 1993.
Gillinov, et al., "Neutrophil Adhesion Molecule Expression During Cardiopulmonary Bypass with Bubble and Membrane Oxygenators" Ann Thorac Surg 56:847–853, 1993.
Gillinov, et al., "Complement and Neutrophil Activation During Cardiopulmonary Bypass: A Study in the Complement—Deficient Dog" Ann Thorac Surg 57:345–352, 1994.
Hackmann, et al. "A Trial of Desmopressin (1—Desamino—8—D—Arginine Vasopressin) to Reduce Blood Loss in Uncomplicated Cardiac Surgery" N Engl J Med 321:1437–1442, 1989.
Haslam, et al., "Complement activation during cardiopulmonary bypass" Anaesthesia, 35:22–26, 1980.
Jones, et al. "Cardiopulmonary bypass and complement activation" Anaesthesia, 37:629–633, 1982.
Kirklin, et al., "Complement and the damaging effects of cardiopulmonary bypass" J Thorac Cardiovasc Surg 86:845–857, 1983.

(List continued on next page.)

Primary Examiner—Lila Feisee
Assistant Examiner—Phillip Gambel
Attorney, Agent, or Firm—Maurice M. Klee; Seth A. Fidel

[57] ABSTRACT

The use of anti-C5 antibodies to reduce the dysfunction of the immune and hemostatic systems associated with extracorporeal circulation procedures, such as, cardiopulmonary bypass procedures, is disclosed. The antibodies have been found to significantly reduce complement activation, platelet activation, leukocyte activation, and platelet-leukocyte adhesion associated with such procedures.

8 Claims, 4 Drawing Sheets

OTHER PUBLICATIONS

Levy et al., "Inflammation and cardiopulmonary bypass" *Can J Anaesth* 40:1009–1015, 1993.

Miyamoto, et al. "Analysis of Complement Activation Profile during Cardiopulmonary Bypass and Its Inhibition by FUT–175" *ASAIO J* 31:508–511, 1985.

Moat, et al. "Complement inhibition may attenuate acute lung injury after cardiopulmonary bypass in pigs" *Am Rev Respir Dis* 145:A845, 1992.

Moat, et al., "Humoral and Cellular Activation in a Simulated Extracorporeal Circuit" *Ann Thorac Surg* 56:1509–1514, 1993.

Mohr, et al., "The hemostatic effect of transfusing fresh whole blood versus platelet concentrates after cardiac operations" *J. Thorac. Cardiovasc. Surg.* 96:530–534, 1988.

Mollnes, et al., "Identification of a Human C5 β—Chain Epitope Exposed in the Native Complement Component but Concealed in the SC5b–9 Complex" *Scand. J. Immunol.* 28:307–312, 1988.

Moongkarndi, et al., "Monoclonal antibodies against the fifth component of human complement" *Immunobiol.* 162:397, 1982.

Moongkarndi, et al., "Immunological and functional properties of two monoclonal antibodies against human C5" 0 *Immunobiol.* 165:323, 1983.

Montz, et al., "Regulation of the Human Autologous T Cell Proliferation by Endogenously Generated C5a" *Cellular Immunol.* 127:337–351, 1990.

Nathan, et al., "Cytokine–induced Respiratory Bur Human Neutrophils: Dependence on Extracellular Matrix Proteins and CD11/CD18 Integrins" *J Cell Biol* 109:1341–1349, 1989.

Nilsson, et al., "Heparin–Coated Equipment Reduces Complement Activation during Cardiopulmonary Bypass in the Pig" *Artif Organs* 14:46–48, 1990.

Øvrum, et al., "Tranexamic acid (Cyklokapron) is not necessary to reduce blood loss after coronary artery bypass operations" *J Thorac Cardiovasc Surg,* 105:78–83, 1993.

Palabrica, et al., "Leukocyte accumulation promoting fibrin deposition is mediated in vivo by P—selectin on adherent platelets" *Nature* 359:848–851, 1992.

Parker, et al., "Changes in serum complement and immunoglobulins following cardiopulmonary bypass" *Surgery* 71:824–827, 1972.

Rinder, et al., "Progressive platelet activation with storage: evidence for shortened survival of activated platelets after transfusion" *Transfusion,* 31:409–414, 1991.

Rinder, et al, "Cardiopulmonary Bypass Induces Leukocyte–Platelet Adhesion" *Blood,* 79:1201–1205, 1992.

Rocha, et al., "Does despmopressin acetate reduce blood loss after surgery in patients on cardiopulmonary bypass?" *Circulation* 77:1319–1323, 1988.

Seghaye, et al., "Complement activation during cardiopulmonary bypass in infants and children" *J Thorac Cardiovasc Surg* 106:978–987, 1993.

Steinberg, et al., "Cytokine and complement levels in patients undergoing cardiopulmonary bypass" *J Thorac Cardiovasc Surg* 106:1008–1016, 1993.

Simpson, et al., "Reduction of Experimental Canine Myocardial Reperfusion Injury by a Monoclonal Antibody (Anti–Mo1, Anti–CD11b) That Inhibits Leukocyte Adhesion" *J Clin Invest* 81:624–629, 1988.

Sonntag and Stein, "Arteriopathic complications during treatment of subarachnoid hemorrhage with epsilonaminocaproic acid" *J Neurosurg* 40:480–484, 1974.

Stanuton, et al., "Primary Structure of ICAM–1 Demonstrates Interaction between Members of the Immunoglobulin and Integrin Supergene Families" *Cell* 52:925–933, 1988.

Staunton, et al., "Functional cloning of ICAM–2, a cell adhesion ligand for LFA–1 homologous to ICAM–1" *Nature* 339:61–64, 1989.

Taggart, et al., "Endotoxemia, Complement, and White Blood Cell Activation in Cardiac Surgery: A Randomized Trial of Laxatives and Pulsatile Perfusion" *Ann Thorac Surg* 57:376–382, 1984.

Tulunay, et al., "Complement (C3, C4) and C—reactive Protein Responses to Cardiopulmonary Bypass and Protamine Administration" *Anaesth Intens Care* 21:50–55, 1993.

Videm, et al., "Different oxygenators for cardiopulmonary bypass lead to varying degrees of human complement activation in vitro" *J. Thorac. Cardiovasc. Surg.,* 97:764–770, 1989.

Videm, et al., "Complement Activation woth Bubble and Membrane Oxygenators in Aortocoronary Bypass Grafting" *Ann Thorac Surg* 50:387–731, 1990.

Videm, et al., "Time for New Concepts About Measurement of Complement Activation by Cardiopulmonary Bypass" *Ann Thorac Surg* 54:725–731, 1992.

Wachtfogel, et al., "Human neutrophil Degranulation During Extracorporeal Circulation" *Blood* 69:324–330, 1989.

Wakefield, et al., "Absence of Complement Mediated Events after Protamine Reversal of Heparin Anticoagulation" *J. Surg. Res.* 51:72–76, 1991.

Wenger, et al., "Loss of platelet fibrinogen receptors during clincial cardiopulmonary bypass" *J Thorac Cardiovasc Surg,* 97:235–239, 1989.

Wurzner, et al., "Complement activation and depletion during LDL–apheresis by heparin–induced extracorporeal LDL–precipitation (HELP)" *European Journal of Clinical Investigation* 21:288–294, 1991.

USE OF C5-SPECIFIC ANTIBODIES FOR REDUCING IMMUNE AND HEMOSTATIC DYSFUNCTIONS DURING EXTRACORPOREAL CIRCULATION

This application is a continuation application of application Ser. No. 08/217,391, filed on Mar. 23, 1994 now abandoned.

The U.S. Government has a paid-up license in this invention and the right in limited circumstances to require the patent owner to license others on reasonable terms as provided for by the terms of Grant No. HL47193 awarded by The National Institutes of Health, Bethesda, Md.

FIELD OF THE INVENTION

The present invention relates to reducing the dysfunction of the immune and hemostatic systems associated with extracorporeal circulation. In particular, the invention relates to the use of antibodies specific to human complement component C5 to effect inhibition of the complement arm of the immune system in order to accomplish such therapeutic prophylaxis.

BACKGROUND OF THE INVENTION

I. Extracorporeal Circulation

Extracorporeal circulation (ECC) of the blood is an important medical technology that is used in a variety of life saving medical procedures. Such procedures include hemodialysis, plasmapheresis, plateletpheresis, leukophereses, extracorporeal membrane oxygenation (ECMO) heparin-induced extracorporeal LDL precipitation (HELP), and cardiopulmonary bypass (CPB). As such, ECC is widely used in modern medical practice.

One of ECC's most common uses is in CPB. Nearly 400,000 CPB surgical procedures are carried out in the United States each year (Rinn, A., *N Enql J Med* 312:119, 1985). The primary medical application of CPB is the facilitation of coronary artery bypass grafting, but it is also utilized during other types of open heart surgery, including procedures to correct congenital heart defects, heart valve disease, or other heart defects. With improvements in surgical techniques and extracorporeal oxygenation, the overall mortality for this procedure is low (1% to 4%) (Allen C. M., *Br Med J* 297:1485, 1988).

Because the most extensive research to date on the effects of ECC on the immune and hemostatic systems has been in the area of CPB, much of the discussion of the detailed effects of ECC presented herein is in connection with CPB. This discussion, however, is not intended to and should not be interpreted as limiting the present invention in any way to CPB.

II. Medical Problems Caused by Extracorporeal Circulation

Although death during ECC procedures is rare, several acute and chronic complications during and subsequent to these procedures result in potentially life-threatening medical problems and cause significant expense to the health care system. Many of these complications have been associated with activation of the immune system, with the complement arm of the immune system playing a particularly important role in the development of inflammation, platelet dysfunction, thrombocytopenia, and other ECC complications. Hemostatic problems during and after ECC can be attributed to several factors, including complement-mediated platelet dysfunction, and can result in both excessive thrombosis and excessive bleeding as platelets first become activated and then become spent and non-functional, and are removed from the circulation. Management of abnormal bleeding associated with CPB often requires re-operation and is frequently associated with excessive, and sometimes inappropriate, blood product administration, occasionally exceeding the available blood supply. In some hospitals, open heart surgery accounts for more than 25% of the total blood product use (Woodman and Harker, *Blood* 76:1690, 1990).

Activation of the complement system occurs when blood plasma contacts foreign surfaces during ECC. Activated complement components can initiate inflammatory responses, with associated vasoconstriction, capillary leakage and platelet activation. A discussion of various of the physiological mechanisms involved in ECC-associated immune and hemostatic dysfunctions is presented below under the heading "Background Physiology."

III. Previous Approaches to Complement Modulation During ECC

The many previous approaches taken in pursuit of controlling activation of the complement system and associated problems arising during ECC illustrate the perceived importance in the medical research community of accomplishing these goals. These approaches have included attempts to alter the mechanical components of CPB circuits, including the use of membrane (as opposed to bubble) oxygenators, and of heparin-coated bypass circuits, as well as various approaches to pharmacological modulation of complement activation. Unfortunately, these efforts have not eliminated the immune and hemostatic system problems associated with ECC, and have, in many cases, themselves been responsible for additional adverse effects.

As mentioned above, foreign surfaces of the ECC circuit cause complement activation. In CPB, the oxygenator constitutes the most significant complement activating surface. Although some studies have shown that membrane oxygenators are associated with less activation of certain complement components than bubble oxygenators, there is no consensus that they cause less overall complement activation during CPB. Rather, complement activation varies with individual oxygenators, whether bubble or membrane (Videm, et al., *Ann Thorac Surg* 50:387, 1990).

Recently, heparin-coated bypass circuits have been shown to reduce complement activation during CPB. Unfortunately, this approach only partially inhibits complement activation (Nilsson, et al., *Artif Organs* 14:46, 1990). No previous pharmacological approach to specifically reduce complement activation during CPB has yielded satisfactory results.

Anti-inflammatory steroid drugs are immunosuppressive agents that can modulate complement function. Although steroid use has been associated with a moderate decrease in complement activation in some studies (Cavarocchi, et al., *J Thorac Cardiovasc Surg* 91:252, 1986), others have found no significant beneficial effect (Miyamoto, et al., *ASAIO J* 31:508, 1985), and the overall immune suppression caused by steroids, and other debilitating side effects associated with steroid administration, further limit their utility in treating ECC patients.

To date, most efforts to modulate the activation of complement in ECC have focused on complement component C3. A recent study evaluated the potential of a soluble recombinant form of human complement receptor type 1 (sCR1, designated BRL55730 by SmithKline Beecham) to reduce complement activation associated with CPB (Gillinov, et al., *Ann Thorac Surg* 55:619, 1993). sCR1 acts by blocking the conversion of complement component C3 into activated components C3a and C3b. Unfortunately, key measures of complement and platelet activation were not evaluated in this study, and the neutrophil and other physiological endpoint results reported were disappointing. In addition, sCR1 blocks C3, and as discussed in detail below, the blockade of C3 activation interrupts the most important antimicrobial actions of the complement system, exposing patients to increased risk of infection.

While ECC clearly causes complement activation, it is also associated with other problems, including kinin generation, loss of coagulation factors by hemodilution, fibrinolysis, liberation of thromboxane $A_2$, and the activation of platelets and neutrophils. Many of these phenomena are, at least in part, secondary consequences of complement activation. Current therapies used to address these specific phenomena have, to date, relied on rather ineffective, broad-based antifibrinolytics and hemostatic agents, examples of which are as follows.

Aprotinin, a broad-based serine proteinase inhibitor (TRASYLOL, Bayer AG) has recently been studied for its effects on CPB associated pathology. Aprotinin inhibits kallikrein, a proteolytic enzyme that attenuates the release of neutrophil elastase, another protease, and diminishes the production of complement component C3a. In the absence of any direct evidence, it has been suggested that aprotinin may also partially inhibit C3 convertase activity (Wachtfogel, et al., *Blood* 69:324, 1989). Although, as mentioned above, there is a consensus in the art that C3a plays a key role in generating ECC-associated immune and hemostatic dysfunctions, CPB-induced activation of platelets, which is (at least in part) secondary to complement activation, is unaffected by aprotinin therapy (Bidstrup, et al., *J Thorac Cardiovasc Surg* 973:364, 1989), and it is clear that platelet dysfunction is directly involved in the pathogenesis of ECC-associated hemostatic problems. The beneficial effects of aprotinin administration are probably related to its ability to inhibit kallikrein, thereby diminishing the proteolytic conversion of plasminogen to plasmin, a key step in blood coagulation. Efficacy of aprotinin in reducing blood loss during CPB has been demonstrated when aprotinin is administered by continuous infusion. Single dose bolus administration of aprotinin, however, has proven ineffective.

Enthusiasm for aprotinin use during CPB has been dampened by recent clinical results showing an increased incidence of perioperative myocardial infarction (16.9% vs. 8.9% for placebo) and a significant incidence of postoperative renal dysfunction associated with aprotinin administration during CPB (Cosgrove, et al., *Ann Thorac Surg* 54:1031, 1992). In this study, postmortem findings in some patients who died after elective coronary operations using aprotinin included acute vein graft occlusions as well as widespread thrombosis in the kidney, native coronary vessels and cerebral vessels. Despite the risks associated with these deleterious clinical events, the benefits of pharmaceutical modulation of adverse effects associated with CPB have recently led to FDA approval of aprotinin for the treatment of patients receiving CPB.

The synthetic lysine analogue EACA (AMICAR, Lederle Laboratories) has been used frequently as an antifibrinolytic agent during CPB. Although EACA is effective in reducing bleeding in a variety of clinical circumstances, its use in CPB has been controversial with regard to its potential to reduce postoperative blood loss (Copeland, et al., *Ann Thorac Surg* 47:88, 1989). Additionally, both arterial and venous thrombosis have complicated EACA therapy in a number of clinical trials and have generally discouraged its clinical use (Sonntag and Stein, *J Neurosurg* 40:480). Tranexamic acid has also been used for its anti-fibrinolytic effect, but has also been associated with excessive thrombotic complications (Orum, et al., *J Thorac Cardiovasc Surg*, 105:78, 1993).

The relatively non-specific hemostatic properties of the synthetic vasopressin analogue, desmopressin acetate, has made it a candidate pharmaceutical agent for treating the hemodynamic alterations associated with CPB. However, randomized double-blind studies of 150 consecutive patients undergoing elective CPB found no significant differences in blood loss or postoperative transfusion requirements in patients receiving desmopressin (Hackmann, et al., *N Engl J Med* 321:1437, 1989; Rocha, et al., *Circulation* 77:1319, 1988).

SUMMARY OF THE INVENTION

In view of the foregoing state of the art, it is an object of the present invention to provide a method for reducing the dysfunction of the immune and hemostatic systems associated with extracorporeal circulation.

The method of the invention involves the use of antibodies to human complement component C5 as a pharmaceutical agent. More particularly, the invention provides for the use of an anti-C5 antibody preparation that binds to native plasma C5, and thereby blocks the generation of activated complement components C5a and C5b from C5. Preferably, the antibody is a monoclonal antibody.

In certain preferred embodiments, the invention is used during CPB. In a further preferred embodiment, the inhibition of dysfunction is accomplished by the administration of a single dose of the anti-C5 antibody preparation.

As shown in the examples presented below, anti-C5 antibodies can completely block important aspects of human complement activity, while maintaining important anti-infective functions of the complement system. In particular, the antibodies completely block the generation of the cytolytic assemblage of activated complement components known as the membrane attack complex. In addition, the antibodies inhibit platelet activation, inhibit leukocyte activation, inhibit platelet-leukocyte interactions, specifically, platelet-monocyte and platelet-polymorphonuclear cell interactions, and inhibit the removal of key glycoproteins from platelet surfaces during extracorporeal circulation of human blood. As a result of these activities, the antibodies help maintain the immune and hemostatic systems in their normal states during ECC.

The accompanying figures, which are incorporated in and constitute part of the specification, illustrate certain aspects of the invention, and together with the description, serve to explain the principles of the invention. It is to be understood, of course, that both the figures and the description are explanatory only and are not restrictive of the invention.

BACKGROUND PHYSIOLOGY

I. Introduction

Figure 1:
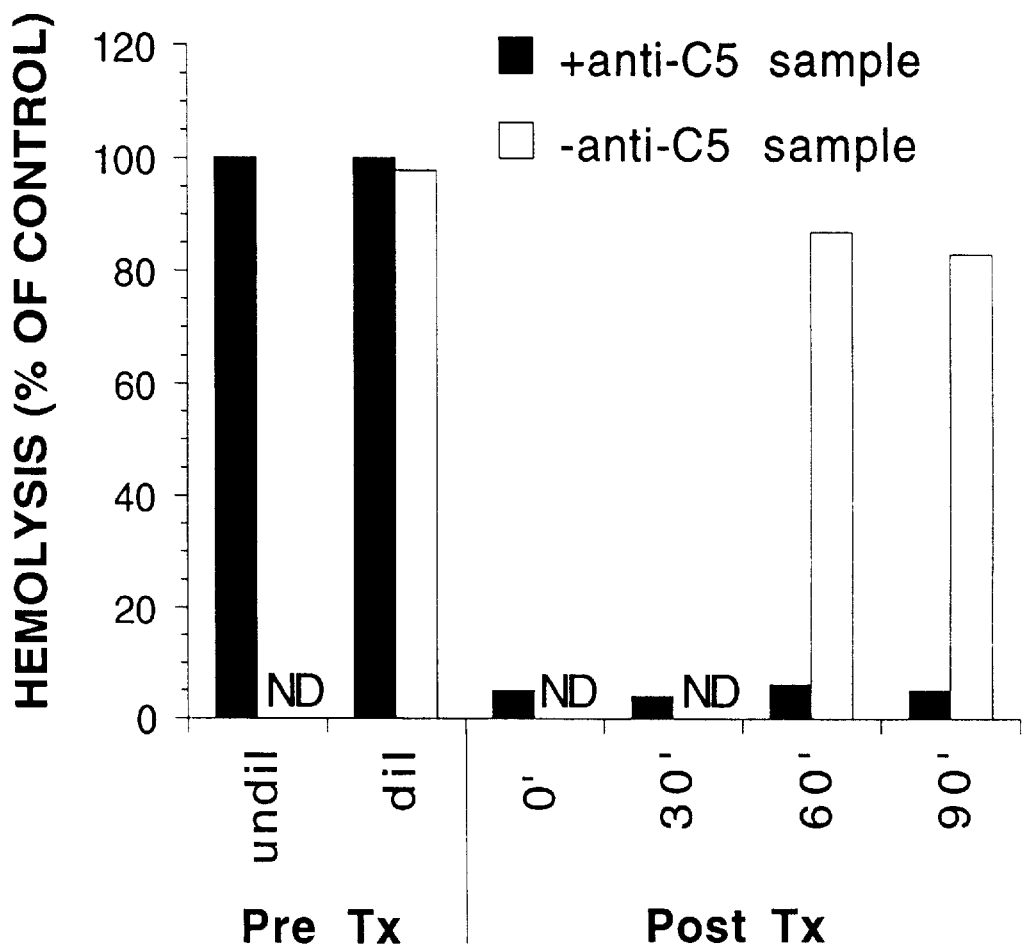
FIG. 1—Hemolytic assay demonstrating anti-C5 monoclonal antibody inhibition of complement activity associated with human blood circulated through an extracorporeal circuit. Assays were performed before the addition of the antibody or the commencement of the CPB circuit ("Pre Tx") using undiluted blood ("undil") and diluted blood ("dil") as described in Example 1. Samples of diluted blood to which the antibody had been added ("Post Tx") were assayed at the times indicated after starting the CPB circuit.

As described above, the present invention relates to inhibition of dysfunctions of the immune and hemostatic systems during ECC. To provide background for the description of the preferred embodiments and the examples presented below, we turn first to general discussions in the context of ECC of the relevant aspects of the immune and hemostatic systems, in particular, certain aspects of the complement arm of the immune system, the cellular arm of the immune system, and the physiology of platelets.

II. Pathophysiology Associated With ECC

A key pathophysiologic change in the blood that is associated with ECC is the rapid activation of the complement cascade. Activation of complement components that mediate inflammation and impact the hemostatic properties of the blood occurs when blood comes in direct contact with the various non-biological components of the ECC circuit (Videm, et al., *J. Thorac. Cardiovasc. Surg.,* 97:764–770, 1989), and can be inhibited to some extent by certain drugs, particularly heparin and protamine, that are administered to patients during ECC procedures (Jones, et al., *Anaesthesia,* 37:629–633, 1982).

Interdependent disturbances in both the immune system and the hemostatic system are seen during CPB and other types of ECC. Many of these changes intersect at the level of platelet function, as the actions of the complement arm of the immune system can result in platelet activation.

In addition to its effects on platelets and the complement arm of the immune system, ECC also effects the cellular arm of the immune system both through effects on leukocytes and through effects on platelet-leukocyte interactions.

(a) Effects of ECC on Platelets

Platelets are anuclear, cellular elements of the blood that are vitally important for the formation of blood clots and the prevention of excessive bleeding. An abnormally severely low platelet count in the blood, a condition known as thrombocytopenia, often results in severe bruising, hemorrhage from mucosal membranes, and considerable loss of blood following surgery or other injury.

Platelet dysfunction has been linked with the contact of platelets with the non-biological surfaces of the extracorporeal oxygenator and the hypothermia associated with CPB. Several other mechanisms, alone or in combination, have also been implicated as contributing to platelet dysfunction. For example, mechanical trauma due to shear stress, surface adherence, and turbulence within the extracorporeal oxygenator may cause fragmentation of platelet membranes. Activated complement components, however, are arguably the most important factors contributing to the platelet dysfunction associated with ECC.

CPB adversely affects platelet count as well as function. Hemodilution during CPB causes platelet counts to rapidly decrease soon after starting CPB, declining to about 50% of preoperative levels. This level of circulating platelets, if occurring in the context of normal individual platelet function, is unlikely to contribute to clinical bleeding. Of greater significance to the development of CPB associated morbidity, however, is the progressive loss of platelet function seen during and after CPB. Within minutes after initiating CPB, bleeding time is prolonged significantly and platelet aggregation is impaired. These changes in bleeding time are independent of platelet count and worsen as CPB progresses. Bleeding times, normally less than 10 minutes, can approach 30 minutes after 2 hours of CPB.

Platelets undergo profound biochemical and morphological alterations when activated by certain stimuli. When caused by stimuli associated with conditions calling for rapid hemostasis, these alterations are associated with the normal functions of platelets. When caused by ECC, pathophysiologic outcomes result. Activation-induced alterations in platelet characteristics include exocytotic degranulation with the release of the contents of various storage organelles, shape changes, and the induction of adhesiveness, aggregation, and thromboxane production.

A specific integral membrane protein, P-selectin (also known as CD62, CD62P, GMP-140, and PADGEM), which is located on the inner surfaces of platelet alpha granules, is translocated to the platelet surface as these organelles turn inside-out during exocytosis. The appearance of P-selectin on the platelet surface thus serves as a marker of platelet activation.

Various lines of evidence suggest that the expression of P-selectin and the temporary depletion or modification of some functional platelet membrane components are key measures of platelet functionality. Several studies have reported significant decreases in the amount of glycoprotein membrane antigens GPIb (CD45b), GPIIb, and GPIIIa on circulating platelets following CPB. The loss of platelet GPIIIa in particular is associated with a reduction in total fibrinogen binding sites. Such surface altered platelets thus demonstrate poor hemostatic capacity.

The removal of platelet membrane glycoproteins may be mediated by the activity of proteolytic enzymes such as plasmin and elastase. The ability of the protease inhibitor aprotinin (discussed above) to minimize glycoprotein (specifically, GPIb) loss after CPB provides evidence implicating direct proteolysis of platelet membrane glycoproteins in the development of platelet dysfunction (Wenger, et al., *J Thorac Cardiovasc Surg,* 97:235, 1989).

Effects of ECC on platelets are particularly significant because platelets can only be activated once, i.e., activation of platelets decreases the number of functional platelets available when platelet functions are subsequently required. The importance of the effects of ECC on platelets is demonstrated by the finding that the impaired hemostasis observed after cardiac operations is mainly attributable to platelet dysfunction (Mohr, et al., *J. Thorac. Cardiovasc. Surg.* 96:530, 1988).

(b) Platelet-Leukocyte Interactions Associated with ECC

The P-selectin molecule, which appears on the membrane surface of activated platelets, is known to mediate the binding of platelets to various types of white blood cells (WBCs, leukocytes) without requiring the activation of the WBCs for such binding to occur. These WBCs include polymorphonuclear leukocytes (PMNs, neutrophils, granulocytes), and monocytes, and the P-selectin mediated binding results in platelet-PMN, and platelet-monocyte conjugate formation (Larsen, et al., *J Biol Chem* 267:11104–11110, 1992; Corral, et al., *Biochem Biophys Res Commun* 172:1349–1353, 1990). One result of such conjugate formation is the removal of platelets from the circulation, a phenomenon that can contribute to the development of thrombocytopenia (Rinde, et al., *Transfusion,* 31:408–414, 1991).

Such leukocyte-platelet adhesion is also believed to be of physiologic importance in the targeting of leukocytes to appropriate inflammatory and/or hemostatic sites and in modulating leukocyte function. The relevance of such targeting has been recently demonstrated in vivo in a baboon model where blockade of P-selectin with a monoclonal antibody resulted in decreased monocyte accumulation on an artificial vascular graft and decreased procoagulant activity (Palabrica, et al., *Nature* 359:848–851, 1992). Such leukocyte-platelet adhesion caused by P-selectin has been found to be induced by CPB (Rinder, et al., *Blood,* 79:1201–1205, 1992).

The modulation of leukocyte function mediated by ECC-associated platelet-leukocyte binding includes the upregulation of the major monocyte procoagulant molecule known as "tissue factor" (TF). Data reported by Catalett, et al., *Blood* 78 (Suppl 1):279a, 1991, suggests that P-selectin induces TF upregulation on monocytes over a four hour period. Such TF upregulation enhances the procoagulatory effects of leukocytes (Altieri, *Blood* 81:569–579, 1993). In a simulated closed-loop CPB model, Kappelmayer, et al., *Circ Res* 72:1075–1081, 1993, have recently demonstrated CPB-associated upregulation of both the quantity and activity of TF on circulating monocytes. The expression of monocyte tissue factor several hours after the conclusion of a CPB procedure, combined with other procoagulatory events occurring during CPB (Evangelista, et al., *Blood* 77:2379–2388, 1991; Higuchi, et al., *Blood* 79:1712–1719, 1992; Weitz, et al., *J Exp Med* 166:1836–1850, 1987) is believed to predispose the patient to late thrombotic events, such as vascular graft re-occlusion.

(c) Other Effects of ECC on Leukocytes

In addition to upregulation of TF on monocytes, CPB-associated upregulation of cell adhesion ligands that contain the $\beta_2$ integrin CD18, in particular, the heterodimeric adhesive ligand that contains CD18 and CD11b (known as CD11b/CD18 or MAC-1), has been described on monocytes and neutrophils (Rinder, et al., *Blood* 79:1201–1205, 1992). Such upregulation is particularly relevant to CPB-induced injury since CD11b/CD18 is responsible for leukocyte adherence to and penetration (diapedesis) through the endothelium via binding to the intercellular adhesion molecules ICAM-1 and ICAM-3 on "activated" endothelium (Staunton, et al., *Cell* 52:925–933, 1988; Staunton, et al., *Nature* 339:61–64, 1989; Furie, et al., *J Immunol* 148:2395–2404, 1992).

In experimental systems, administration of monoclonal antibodies blocking the activity of CD11b/CD18 has been shown to prevent reperfusion injury (Simpson, et al., *J Clin Invest* 81:624–629, 1988; Arnaout, *Blood* 75:1037–1050, 1990; Dreyer, et al., *Circ* 84:400–411, 1991). In addition, increased CD11b/CD18 expression on leukocytes has been linked to complications associated with hemodialysis (Arnaout, et al., *N Engl J Med* 312:457, 1985). Thus, CD11b/CD18 may contribute to ECC associated medical problems.

In addition to the foregoing, the CD11b moiety functions as the receptor for complement component iC3b and for elements of the contact dependant soluble coagulation system, including fibrinogen, fibronectin, and Factor X (Altieri, et al.,*Proc Natl Acad Sci USA* 85:7462–7465, 1988; Nathan, et al., *J Cell Biol* 109:1341–1349, 1989). The interactions of CD11b with fibrinogen may be of particular importance to ECC-associated pathology, since, as discussed above, the platelet surface glycoprotein complex GPIIb-IIIa is also associated with fibrinogen binding, thus providing a potential means for platelet-leucocyte adhesion, i.e., via a CD11b—fibrinogen—GPIIb-IIIa linkage (Altieri, et al., *Proc Natl Acad Sci USA* 85:7462–7465, 1988). Induction of an inflammation-associated respiratory burst in granulocytes in response to a variety of cytokines also appears to require CD11b/CD18 in the local adherent microenvironment.

Thus this $\beta_2$ integrin complex exerts its effects at critical junctures of the complement system, the cellular immune system, and the soluble cellular coagulation pathway. CD11b/CD18 expression on leukocyte surfaces can thus be assayed as a predictive indicator related to the probability of the occurrence of complement, immune, and coagulation associated events.

(d) The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade progresses via the classical pathway or the alternative pathway. These pathways share many components, and while they differ in their initial steps, they converge and share the same "terminal complement" components responsible for the activation, attack, and destruction of target cells.

The classical complement pathway is typically initiated by antibody recognition of and binding to an antigenic site on a target cell. The alternative pathway is usually antibody independent, and can be initiated by certain molecules on pathogen surfaces. Both pathways converge at the point where complement component C3 is cleaved by an active protease (which is different in each pathway) to yield C3a and C3b. Other pathways activating complement attack can act later in the sequence of events leading to various aspects of complement function.

C3a is an anaphylotoxin (see below). C3b binds to bacterial and other cells and tags them for removal from the circulation. (C3b in this role is known as opsonin.) The opsonic function of C3b is considered to be the most important anti-infective action of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to *Neisseria* infection, and then only somewhat more prone (Fearon, in *Intensive Review of Internal Medicine,* 2nd Ed. Fanta and Minaker, eds. Brigham and Women's and Beth Israel Hospitals, 1983).

C3b also forms a complex with other components unique to each pathway to form classical or alternative C5 convertase, which cleaves C5 into C5a and C5b. C3 is thus regarded as the central protein in the complement reaction sequence since it is essential to both the alternative and classical pathways (Wurzner, et al., *Complement Inflamm* 8:328–340, 1991). This property of C3b is regulated by the serum protease Factor I, which acts on C3b to produce iC3b. While still functional as opsonin, iC3b cannot form an active C5 convertase.

C5a is another anaphylatoxin (see below). C5b combines with C6, C7, and C8 to form the C5b-8 complex at the surface of the target cell. Upon binding of several C9 molecules, the membrane attack complex (MAC, C5b-9, terminal complement complex—TCC) is formed. When sufficient numbers of MACs insert into target cell membranes the openings (MAC pores) they create mediate rapid osmotic lysis of the target cells. Lower, non-lytic concentrations of MACs can produce other effects In particular, membrane insertion of small numbers of the C5b-9 complexes into endothelial cells and platelets can cause deleterious cell activation. In some cases activation may precede cell lysis.

Certain aspects of the mechanism of C5b-9 mediated platelet activation have been described (Sims, et al., *J Biol Chem,* 264:19228, 1989). Sublytic concentrations of MAC pores on platelet surfaces allow an influx of extracellular calcium ions into the platelet. The resulting elevated levels of intraplatelet calcium ions act as an activating signal and induce the surface expression of P-selectin that is characteristic of activated platelets. Since, as described above, P-selectin mediates platelet-monocyte binding, and such binding triggers the release of tissue factor from monocytes, the formation of MAC pores in platelet surface membranes can have deleterious effects on patients. For example, platelet activation by MAC pores can predispose a CPB patient to late thrombotic events, such as vascular graft re-occlusion.

As mentioned above, C3a and C5a are anaphylatoxins. These activated complement components can trigger mast cell degranulation, which releases histamine and other mediators of inflammation, resulting in smooth muscle contraction, increased vascular permeability, leukocyte activation, and other inflammatory phenomena. C5a also functions as a chemotactic peptide that serves to attract pro-inflammatory granulocytes to the site of complement activation. In addition, direct activation of endothelial cells by C5a induces the release of the coagulation-inhibiting glycoprotein heparan sulfate. The release of heparan sulfate can have the effect of decreasing the levels of this coagulation-inhibiting molecule at the endothelial cell surface, with the consequence of increasing the thrombogenic potential of the endothelial cell surface (Platt, et al., *J Exp Med* 171:1363, 1990).

(e) Complement and Platelet Function and ECC

The activation and consumption of complement components during ECC, specifically CPB, is evidenced by levels of hemolytic complement activity that are much lower at the end of CPB than can be explained by hemodilution alone. A rapid effect on complement components accompanies the initiation of extracorporeal circulation; evidence of alternative pathway activation is observed minutes after the onset of CPB. Classical pathway activation has also been observed during CPB (Haslam, et al., *Anaesthesia* 35:22, 1980).

The levels of C3a anaphylatoxin have been found to increase dramatically during CPB, and there is a strong statistical association between elevated C3a levels and post-operative organ system dysfunction manifest by impairment and/or failure of cardiac, renal and pulmonary systems, bleeding diathesis, and the need for artificial ventilation (Kirklin, et al., *J Thorac Cardiovasc Surg* 86:845–847, 1983). This association has led to the belief that C3a is a key mediator of the deleterious effects linked to complement activation during CPB.

It is well established that platelets can be activated by the assembly of terminal complement components C5b-9 on their surfaces. The assembly of these complement components on platelets is known to occur during ECC (Finn, et al., *J Thorac Cardiovasc Surg,* 105:234, 1993). Complement-mediated platelet activation, in turn, leads to alpha-granule release, increased expression of P-selectin, and the loss of GPIb. The generation of products of complement activation such as C3a, C5a, and C5b-9 further results in platelet membrane vesiculation and consequent microparticle formation.

Other damaging effects of complement activation during CPB can include the activation of granulocytes, leading to partial degranulation and up-regulation of CD11b/CD18, and to damage to organs. Such damaging effects are largely due to the actions of certain products of complement activation, specifically the anaphylatoxins C3a and C5a, which, in turn, can be converted to desArg forms with altered activity levels by plasma carboxypeptidase. These activated complement components cause activation and aggregation of neutrophils. Such activated cells, in turn, accumulate in the pulmonary vessels and vascular beds, as has been demonstrated by serial biopsies of lung tissue before and after CPB (Howard, et al., *Arch Surg,* 123:1496–1501, 1988). Liver, brain and pancreas, also suffer such damage, which can result in postoperative dysfunction of these organs.

Although circumstantial data indicates that activated complement components C3a, C5a, and C5b-9 play a critical role in the pathophysiology of CPB, to date definitive evidence has been lacking. Additionally, the relative contribution of these individual complement components to the generation of the inflammatory process associated with CPB has remained undefined.

DESCRIPTION OF THE PREFERRED EMBODIMENTS

As discussed above, the present invention relates to the use of anti-C5 antibodies in ECC. More generally, the invention relates to the use of anti-C5 antibodies in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artifical or foreign organ, tissue, or vessel into the blood circuit of a patient.

Conduit materials which have the foregoing effects on blood include those now known in the art as well as those which may be developed in the future. Such materials include synthetic materials such as the various forms of plastics and synthetic polymers used in CPB circuits, hemodialysis circuits, vascular grafts, and artificial organs, as well as biological materials of xenogeneic origin.

The anti-C5 antibody is used to reduce at least one of complement activation, platelet activation, leukocyte activation, or platelet-leukocyte adhesion resulting from the circulation of the patient's blood through such a conduit.

Reduction of complement activation can be measured by methods well known in the art, for example, by the chicken erythrocyte hemolysis method described below in Example 1. Preferably, a sufficient amount of antibody is used to reduce the increase in plasma hemolytic activity resulting from complement activation caused by contact with the conduit by at least 50%.

Reduction of platelet activation can be measured by various methods well known in the art, for example, by immunofluorescence analysis of the expression of platelet activation markers GPIIb-IIIa or P-selectin by the methods described below in Examples 1 and 4. Again, it is preferred to use a sufficient amount of antibody so as to achieve at least a 50% reduction in the increase in the expression of at least one of the platelet activation markers resulting from contact with the conduit.

Reduction of leukocyte activation can be measured by various methods well known in the art, for example, by immunofluorescence analysis of the expression of the leukocyte activation marker CD11b/CD18. As described in Example 4, the expression of this marker can be determined by the measurement of CD11b expression. Again, it is preferred to use a sufficient amount of antibody so as to achieve at least a 50% reduction in the increase in the expression of the leukocyte activation marker by at least one type of leukocyte, e.g., PMNs, resulting from contact with the conduit.

Reduction of the levels of platelet-leukocyte adhesion, specifically platelet-monocyte and platelet-neutrophil adhesion, can be measured by the fluorescence analysis techniques described below in Example 4, e.g., as the percent increase in leukocytes that read as GPIb or GPIIb/IIIa positive. Again, it is preferred to use a sufficient amount of antibody so as to achieve at least a 50% reduction in the increase in the percentage of GPIb or GPIIb/IIIa positive monocytes or neutrophils resulting from contact with the conduit.

To achieve the desired reductions, the anti-C5 antibodies can be administered in a variety of unit dosage forms. The dose will vary according to, e.g., the particular antibody, the manner of administration, the particular procedure being performed and its duration, the nature of the conduit or conduits used in the procedure, the overall health, condition, size, and age of the patient, and the judgment of the prescribing physician. Dosage levels for human subjects are generally between about 1 mg per kg and about 100 mg per kg per patient per treatment, and preferably between about 5 mg per kg and about 50 mg per kg per patient per treatment. In some cases, only a single dose of the anti-C5 antibody can be administered to the patient in order to achieve a therapeutic effect.

The anti-C5 antibody is preferably administered prior to contact of the blood with the conduit. In addition, administration can be continued for as long as the blood is in contact with the conduit, and even after that time, if desired. In the case of prior administration, a single dose can be used. For administration continuing throughout the procedure and/or thereafter, periodic doses or a continuous infusion of the anti-C5 antibody can be used.

A typical procedure, in accordance with the present invention, thus includes the following steps. The patient is prepared for surgery in accordance with standard practice, and within an hour of the commencement of surgery, but generally before the commencement of the surgery, a first dose of the pharmaceutical preparation containing the anti-C5 antibody is given. Usually, as determined by the judgement of the physician, a series of doses may also be administered during and after the procedure. Alternatively, during and after the procedure is conducted, levels of serum complement activity available in the patient's blood are monitored using the techniques set forth below in Example 1 to determine if additional doses are required, with such doses being administered as required to maintain at least a 50% reduction, and preferably about a 95% reduction of serum complement activity.

Administration of the anti-C5 antibodies will generally be performed by an intravascular route, e.g., via intravenous infusion by injection. Other routes of administration may be used if desired. Formulations suitable for injection are found in *Remington's Pharmaceutical Sciences*, Mack Publishing Company, Philadelphia, Pa., 17th ed. (1985). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like.

The formulations (Pharmaceutical agents) of the invention can be distributed as articles of manufacture comprising packaging material and the anti-C5 antibody. The packaging material will include a label which indicates that the formulation is for use in association with an extracorporeal circulation procedure, e.g., a cardiopulmonary bypass procedure.

The anti-C5 antibody is preferably a monoclonal antibody, although polyclonal antibodies produced and screened by conventional techniques can also be used if desired. Preferably, the anti-C5 antibodies are immunoreactive against epitopes on the beta chain of purified human complement component C5 (i.e., the part of the C5 molecule that becomes C5b) and are capable of blocking the conversion of C5 into C5a and C5b by C5 convertase. This capability can be measured using the techniques described in Wurzner, et al., *Complement Inflamm* 8:328–340, 1991. The amount of reduction of C5 convertase activity is preferably at least about 50% of the increase in convertase activity resulting from contact with the conduit.

Hybridomas producing monoclonal antibodies reactive with complement component C5 can be obtained according to the teachings of Sims, et al., U.S. Pat. No. 5,135,916. As discussed therein, antibodies are prepared using purified components of the complement membrane attack complex as immunogens. In accordance with the present invention, complement component C5 or C5b is preferably used as the immunogen. In accordance with the present invention, the antibodies preferably should prevent the cleavage of C5 to form C5a and C5b, thus preventing the generation of the anaphylatoxic activity associated with C5a and preventing the assembly of the membrane attack complex associated with C5b. In a particularly preferred embodiment, these anti-C5 antibodies will not impair the opsonization function associated with the activation of complement component C3 by a C3 convertase. Plasma C3 convertase activity can be measured by assaying plasma for the presence of C3a as described below in Example 2. Preferably, the anti-C5 antibody produces essentially no reduction in plasma C3a levels.

General methods for the immunization of animals (in this case with C5 or C5b), isolation of antibody producing cells, fusion of such cells with immortal cells (e.g., myeloma cells) to generate hybridomas secreting monoclonal antibodies, screening of hybridoma supernatants for reactivity of secreted monoclonal antibodies with a desired antigen (in this case C5 or C5b), the preparation of quantities of such antibodies in hybridoma supernatants or ascites fluids, and for the purification and storage of such monoclonal antibodies, can be found in numerous publications. These include: Coligan, et al., eds. *Current Protocols In Immunology*, John Wiley & Sons, New York, 1992; Harlow and Lane, *Antibodies. A Laboratory Manual*, Cold Spring Harbor Laboratory, New York, 1988; Liddell and Cryer, *A Practical Guide To Monoclonal Antibodies*, John Wiley & Sons, Chichester, West Sussex, England, 1991; Montz, et al., *Cellular Immunol.* 127:337–351, 1990; Wurzner, et al., *Complement Inflamm* 8:328–340, 1991; and Mollnes, et al., *Scand. J. Immunol.* 28:307–312, 1988.

As used herein, the term "monoclonal antibodies" refers to immunoglobulins produced by a hybridoma and antigen binding fragments (e.g., Fab' preparations) of such immunoglobulins, as well as to recombinantly expressed antigen binding proteins, including immunoglobulins, chimeric immunoglobulins, "humanized" immunoglobulins, antigen binding fragments of such immunoglobulins, single chain antibodies, and other recombinant proteins containing antigen binding domains derived from immunoglobulins. Publications describing methods for the preparation of such monoclonal antibodies, in addition to those listed immediately above, include: Reichmann, et al., *Nature*, 332:323–327, 1988; Winter and Milstein, *Nature*, 349:293–299, 1991; Clackson, et al., *Nature*, 352:624–628, 1991; Morrison, *Annu Rev Immunol*, 10:239–265, 1992; Haber, *Immunol Rev*, 130:189–212, 1992; and Rodrigues, et al., *J Immunol*, 151:6954–6961, 1993.

Without intending to limit it in any manner, the present invention will be more fully described by the following examples.

EXAMPLE 1

Anti-C5 Monoclonal Antibody Inhibition of Complement Activity During Extracorporeal Circulation The effects of a monoclonal antibody raised to human C5 on complement activation was evaluated using a closed-loop CPB model for the extracorporeal circulation of human blood. The C5 monoclonal antibody was raised in mice against purified human C5 protein (Wurzner, et al., *Complement Inflamm* 8:328–340, 1991) and was propagated, recovered and purified as an IgG fraction from mouse ascites fluid (*Antibodies. A Laboratory Manual*, Cold Spring Harbor Laboratory, New York, 1988; *Current Protocols In Immunology*, John Wiley & Sons, New York, 1992).

To carry out these experiments, 300 ml of whole human blood was drawn from a healthy human donor and additionally a 1 ml sample was removed as a control sample for later analysis. The blood was diluted to 600 ml by the addition of Ringer's lactate solution containing 10U/ml heparin. The blocking anti-C5 mAb (30 mg in sterile PBS) was added to the diluted blood to a final concentration of 50 $\mu$g/ml. In a control experiment, an equal volume of sterile PBS was added to the diluted blood. The blood was then used to prime the extracorporeal circuit of a COBE CML EXCEL membrane oxygenator CPB machine (Cobe BCT, Inc., Lakewood, Colo.)and the circuit was started. The circuit was cooled to 28° C. and circulated for 60 min. The circuit was then warmed to 37° C. and circulated for an additional 30 min. The experiment was then terminated. Samples were taken at several time points and evaluated for complement activity (FIG. 1).

At each time point an aliquot of whole blood was taken, divided into 3 samples and A) diluted 1:1 in 2% paraformaldehyde in PBS to evaluate platelet and blood cell activation parameters (Example 4); B) centrifuged to remove all cells and plasma diluted 1:1 in Quidel sample preservation solution (Quidel Corporation, San Diego, Calif.) and stored at −80° C. to evaluate C3a and C5b-9 generation (Examples 2 and 3, respectively), and C) centrifuged to remove all cells and plasma frozen at −80° C. for hemolytic assays to evaluate complement activity (Example 1).

To evaluate complement activity, the frozen plasma samples were thawed and hemolytic assays were performed as follows. Chicken erythrocytes were washed well in GVBS (Rollins, et al.,*J Immunol* 144:3478–3483, 1990) and resuspended to $2\times10^8$/ml in GVBS. Anti-chicken erythrocyte antibody (IgG fraction of anti-chicken-RBC antiserum, Intercell Technologies, Hopewell, N.J.) was added to the cells at a final concentration of 25 $\mu$g/ml and the cells were incubated for 15 min. at 23° C. The cells were washed 2x with GVBS and $5\times10^6$ cells were resuspended in a final volume of 130 $\mu$l GVBS containing 5% plasma. After incubation for 30 min. at 37° C., % hemolysis was calculated relative to a human serum control sample (FIG. 1). Hemolysis was determined by spinning the cells down and measuring released hemoglobin in the supernatant as the optical density at 415 nm.

As can be seen in FIG. 1, addition of the anti-C5 antibody to the extracorporeal circuit resulted in a 95% reduction in serum complement activity. The complement activity remained inhibited throughout the course (90 minutes) of the experiment.

EXAMPLE 2

Generation of C3a During Extracorporeal Circulation

The fresh frozen plasma samples that had previously been diluted in Quidel sample preservation solution (see Example 1) were assayed for the presence of the complement split product C3a by using the Quidel C3a EIA kit (Quidel Corporation, San Diego, Calif.). These measurements were carried out according to the manufacturers specifications. C3a released is expressed in ng/well as determined by comparison to a standard curve generated from samples containing known amounts of human C3a.

Figure 2:
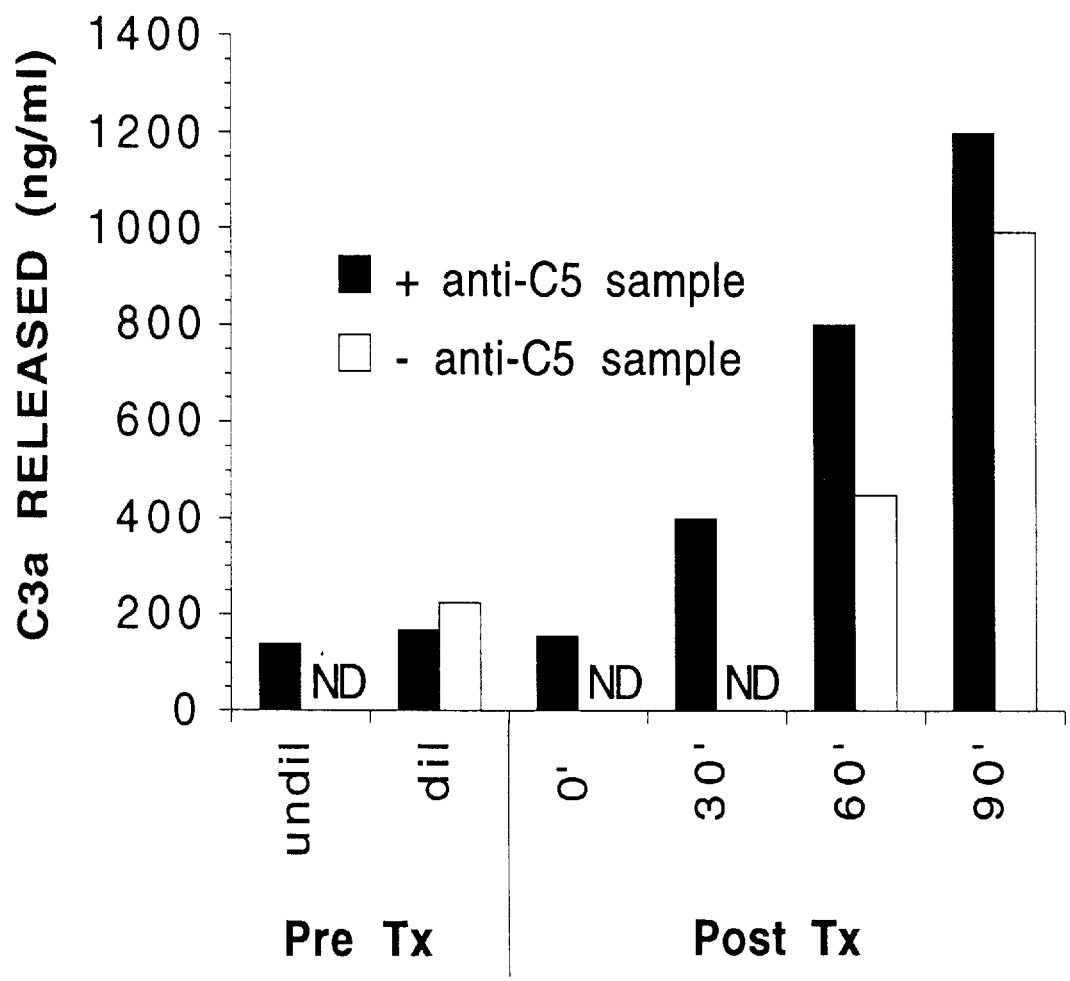
FIG. 2—Assay of levels of complement component C3a demonstrating that the generation of complement component C3a in whole human blood circulated through an extracorporeal circuit is not inhibited by the addition of an anti-C5 monoclonal antibody to such whole blood. Assays were performed before the addition of the antibody or the commencement of the CPB circuit ("Pre Tx") using undiluted blood ("undil") and diluted blood ("dil") as described in Example 1. Samples of diluted blood to which the antibody had been added ("Post Tx") were assayed at the times indicated after starting the CPB circuit.

As seen in FIG. 2, addition of the anti-C5 antibody had no effect on the production of C3a during the CPB experiment. C3a generation was dramatically increased during the final 30 min. of the experiment and correlates with sample warming.

EXAMPLE 3

Prevention of the Generation of C5b-9 During Extracorporeal Circulation

Fresh frozen plasma samples that had been previously diluted in Quidel sample preservation solution (see Example 1) were assayed for the presence of the terminal human complement complex C5b-9 using the Quidel C5b-9 kit (Quidel Corporation, San Diego, Calif.). The amount of C5b-9 in each sample was determined using the manufacturers specifications and is expressed in arbitrary absorbance units (AU).

Figure 3:
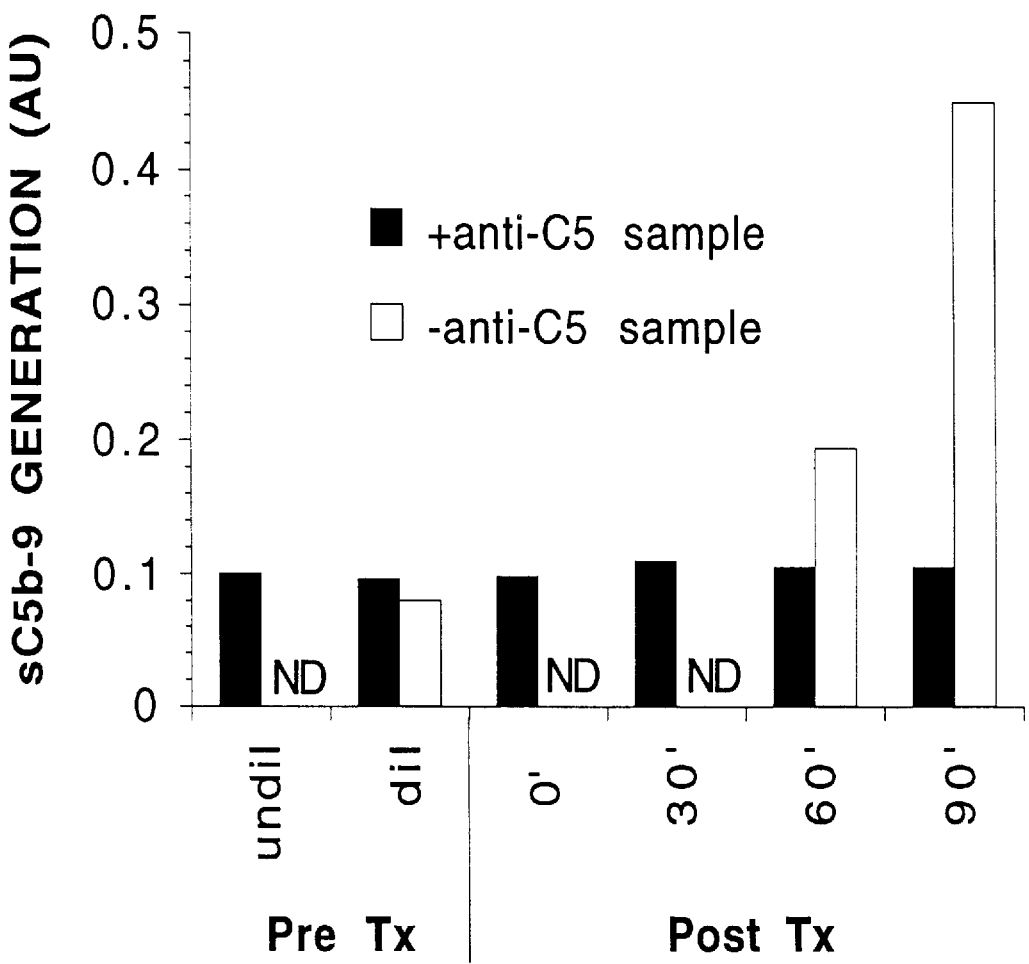
FIG. 3—Assay of the levels of soluble C5b-9 in human blood circulated through an extracorporeal circuit demonstrating that the addition of an anti-C5 monoclonal antibody to such whole blood inhibits the formation of the C5b-9 terminal complement assembly. Assays were performed before the addition of the antibody or the commencement of the CPB circuit ("Pre Tx") using undiluted blood ("undil") and diluted blood ("dil") as described in Example 1. Samples of diluted blood to which the antibody had been added ("Post Tx") were assayed at the times indicated after starting the CPB circuit.

As can be seen in FIG. 3, the anti-C5 antibody completely inhibited C5b-9 generation during extracorporeal circulation so that C5b-9 levels during the full course of the run were equivalent to control ($t_0$) time points. The results of this experiment and those of Examples 1 and 2 show that the addition of an anti-C5 mAb during extracorporeal circulation effectively inhibits both complement hemolytic activity (FIG. 1) and C5b-9 generation (FIG. 3), but not C3a generation (FIG. 2).

EXAMPLE 4

Prevention of Platelet and Leukocyte Activation and Adhesion During Extracorporeal Circulation Paraformaldehyde fixed samples of whole blood taken at T=0 and T=90 minutes during the extracorporeal circulation experiment (see Example 1) were washed, labeled with fluorescent antibodies directed against various cell surface marker molecules, and analyzed by flow cytometry (FACS). The primary antibodies used in these experiments were anti-GPIIb-IIIa (clone RUUSP2.41, AMAC, Inc., Westbrook, Me.); anti-CD11b (Anti-CR3 (leu-15) clone D12, Becton-Dickinson Immunocytometry Systems, San Jose, Calif.); anti-P-selectin, (1E3 obtained from Dr. Kenneth Ault, Maine Medical Center Research Institute, Portland, Me.); anti-GPIb (CD42b), (IOP42b clone SZ2, AMAC, Inc., Westbrook, Me.), and anti-CD45 (a marker for both monocytes and PMNs, which are distinguished by the forward and side scatter characteristics of the FACS profiles of the CD45 positive cells) (Anti-Leucocyte (HLe-1; CD45) clone 2D1, Becton-Dickinson Immunocytometry Systems, San Jose, Calif.). The percent change in surface expression of various cell surface receptors (Platelet GPIb, Platelet GPIIb-IIIa, P-selectin, CD11b) was calculated by comparison of mean FL-1 values obtained for each antibody by the following calculation: T=90/ T=0×100.

Platelet monocyte binding (PLT/MONO) and platelet neutrophil binding (PLT/PMN) was determined by calculating the percentage of neutrophils or monocytes that read positive for the platelet-specific receptor GPIb.

Figure 4:
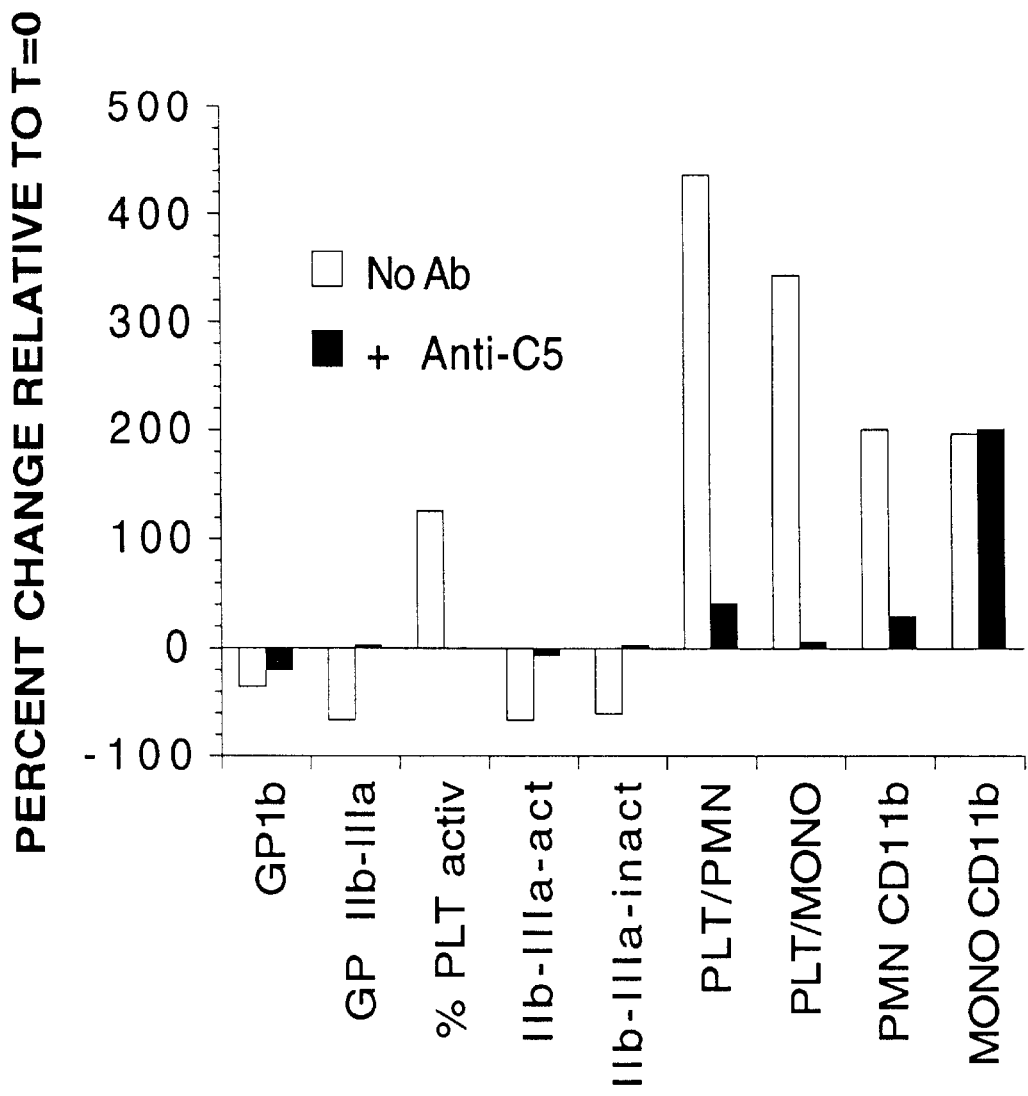
FIG. 4—FACS analysis of levels of GPIb ("GP1b") on all platelets, GPIIb-IIIa on all platelets (regardless of P-selectin expression, "GPIIb-IIIa"), P-selectin on all platelets ("% PLT activ"), GPIIb-IIIa on P-selectin positive platelets ("IIb-IIIa-act"), GPIIb-IIIa on P-selectin negative platelets ("IIb-IIIa-inact"), platelet neutrophil binding ("PLT/PMN"), platelet monocyte binding ("PLT/MONO"), neutrophil CD11b levels ("PMN CD11b"), and monocyte CD11b levels ("MONO CD11b"), demonstrating inhibition of all except the last of these parameters by the addition of an anti-C5 monoclonal antibody to whole human blood during ECC.

As can be seen in FIG. 4, the addition of anti-C5 antibody to the blood in the ECC circuit had a dramatic effect on various aspects of platelet and blood cell activation. In the presence of the anti-C5 antibody, platelets retained 50% more GPIb as compared to non-treated controls. Similarly, platelets retained virtually all of their cell surface GPIIb-IIIa while untreated platelets lost 80% of this receptor. Platelet activation as determined by expression of P-selectin was completely inhibited by the addition of the anti-C5 antibody. Conjugate formation by platelets and monocytes and/or platelets and neutrophils was inhibited by addition of the anti-C5 antibody. Additionally, expression of CD11b on neutrophils was blocked by 75% by anti-C5 while CD11b expression on monocytes was unaffected.

These results show that the anti-C5 antibody is a potent inhibitor of complement-induced platelet activation, leukocyte activation, specifically; PMN activation, and platelet-leukocyte adhesion during extracorporeal circulation and that terminal complement components, and not C3a, are largely responsible for complement-mediated inflammation and platelet dysfunction.

Throughout this application various publications, patents, and patent applications are referred to. The teachings and disclosures of these publications, patents, and patent applications in their entireties are hereby incorporated by reference into this application to more fully describe the state of the art to which the present invention pertains.

Although preferred and other embodiments of the invention have been described herein, further embodiments may be perceived by those skilled in the art without departing from the scope of the invention as defined by the following claims.

What is claimed is:

1. A method for performing a therapeutic procedure on a patient comprising:

(a) passing circulating blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion in the patient's blood; and (b) introducing an antibody that specifically binds to complement component C5 and has the following effects when added to blood passing through such a conduit in vitro:
      (1) the antibody reduces complement activation;
      (2) the antibody reduces leukocyte activation; and
      (3) the antibody produces essentially no reduction in the generation of plasma C3a;

into the patient's bloodstream in an amount effective to reduce at least one of complement activation, platelet activation, leukocyte activation, or platelet-leukocyte adhesion resulting from passage of the circulating blood through said conduit, wherein step (a) occurs in at least one temporal relation to step (b) selected from the group consisting of before step (b), during step (b), and after step (b).

2. The method of claim 1 wherein the antibody reduces the conversion of complement component C5 into complement components C5a and C5b.

3. The method of claim 1 wherein the antibody specifically binds to C5b.

4. The method of claim 1 wherein the therapeutic procedure is an extracorporeal circulation procedure.

5. The method of claim 4 wherein the extracorporeal circulation procedure is a cardiopulmonary bypass procedure.

6. The method of claim 1 wherein the antibody is a monoclonal antibody.

7. The method of claim 4 wherein the antibody is a monoclonal antibody.

8. The method of claim 5 wherein the antibody is a monoclonal antibody.

* * * * *